United States Patent

Hugelshofer

[11] 4,187,984
[45] Feb. 12, 1980

[54] METALLIZING GUN FOR APPLYING SPRAYED METAL

[75] Inventor: Max Hugelshofer, Dietlikon, Switzerland

[73] Assignee: Etablissement Dentaire Ivoclar, Liechtenstein

[21] Appl. No.: 896,850

[22] Filed: Apr. 17, 1978

[30] Foreign Application Priority Data

Apr. 22, 1977 [CH] Switzerland ............... 5015/77

[51] Int. Cl.² ................................. B05B 1/24
[52] U.S. Cl. ............................ 239/13; 239/82
[58] Field of Search ............ 239/79, 80, 81, 82, 239/73, 74, 13

[56] References Cited

U.S. PATENT DOCUMENTS

| | | |
|---|---|---|
| 1,754,382 | 4/1930 | Baracate .................. 239/82 X |
| 1,880,331 | 10/1932 | Rapp ......................... 239/82 |
| 2,434,911 | 1/1948 | Denyssen .................. 239/82 |
| 2,530,186 | 11/1950 | Trimm et al. ............. 239/82 |
| 2,663,590 | 12/1953 | Wyatt ....................... 239/74 |
| 3,976,247 | 8/1976 | Carnelo ................... 239/79 X |

Primary Examiner—John J. Love
Attorney, Agent, or Firm—Sprung, Felfe, Horn, Lynch & Kramer

[57] ABSTRACT

Metals with a relatively low melting point can be sprayed in the form of droplets which coalesce to form a coating. A metallizing gun is used for this purpose which comprises a thinwalled container of steel for the liquid metal which is surrounded by a massive block consisting of an alloy of a thermally conductive metal, which contains an electric heating element and a temperature sensor and whose external side serves to mount air ducts which transmit heat to the block and connect to the spray nozzle.

10 Claims, 3 Drawing Figures

METALLIZING GUN FOR APPLYING SPRAYED METAL

BACKGROUND OF THE INVENTION

This invention relates to a metallizing gun for applying sprayed metal which has a melting point below 350° C., which is liquified by an electric heating means provided in the metallizing gun and which is atomized into droplet form by means of pre-heated compressed air.

Special metal alloys, which have been developed for such metal spraying procedures, are commercially available under the name "Cerro alloys" (alloys of bismuth). This metal spraying technique is employed in particular in the manufacture of moulds. Similar to the galvanoplastic technique, it produces exact but thinwalled mould shells with a faithful reproduction of surface details which are frequently backfilled for subsequent use. The present invention relates to a metallizing gun designed to execute this process.

In a metallizing gun of this type, the metal must be liquified in a container belonging to the gun and then maintained at the correct temperature. Moreover, the air required to spray the metal must be preheated also.

In former practice two heating elements with separate thermostatic controls were employed. It is important to maintain the correct temperature. Overheating the metal alloy is detrimental as is an overheating of the heating elements themselves. Simple thermostats, however, normally do not shut off until after the predetermined temperature has been exceeded. This in turn means that the alloy is usually overheated briefly. The element which heats up the air does not operate satisfactorily due to its inherent inertia. It is still cold at the beginning of the metallizing process, for example, and at the conclusion of the process, when the stream of air terminates, it overheats.

SUMMARY OF THE INVENTION

The object of the present invention is to obviate these prior art drawbacks. In particular, the object of the invention is to provide a heating system which can be better adapted to the process and which can be better regulated.

This object is accomplished in accordance with the invention by the metallizing gun which was explained in detail at the outset and which is characterized by a thinwalled steel container for the molten metal surrounded by a massive block of a thermally conductive metal alloy, containing an electric heating element and a temperature sensor, air ducts which connect to the spray nozzle and which transmit heat to the block being mounted on the external side of said container.

The thinwalled container expediently consists of chromium steel and an aluminum alloy is advantageously used as the thermally conductive metal.

It is advantageous if the massive block is accommodated in a plastic housing with an interposed layer of heat insulation material or air because those parts of the metallizing gun which the operator holds in his hand then remain relatively cool. Another advantage of the metallizing gun is that the temperature can be regulated more exactly with the aid of the temperature sensor than was hitherto possible with electric regulators. The massive block, preferably consisting of an aluminum alloy, makes the heat content less dependent on the amount of the molten alloy, permits the simple and easy mounting of the temperature sensor and permits the air required for spraying to be heated without necessitating a separate heating element. The aluminum block results in improved heat distribution along the entire path of the metal.

BRIEF DESCRIPTION OF THE DRAWING

One embodiment of the invention is shown in the drawing and will be explained in more detail with reference to the description which follows. In the drawing:

FIG. 3 is a section along line III—III in FIG. 1.

FIG. 4 is a sectional view taken along the line IV—IV of FIG. 3.

DESCRIPTION OF THE PREFERRED EMBODIMENT

Figure 1:
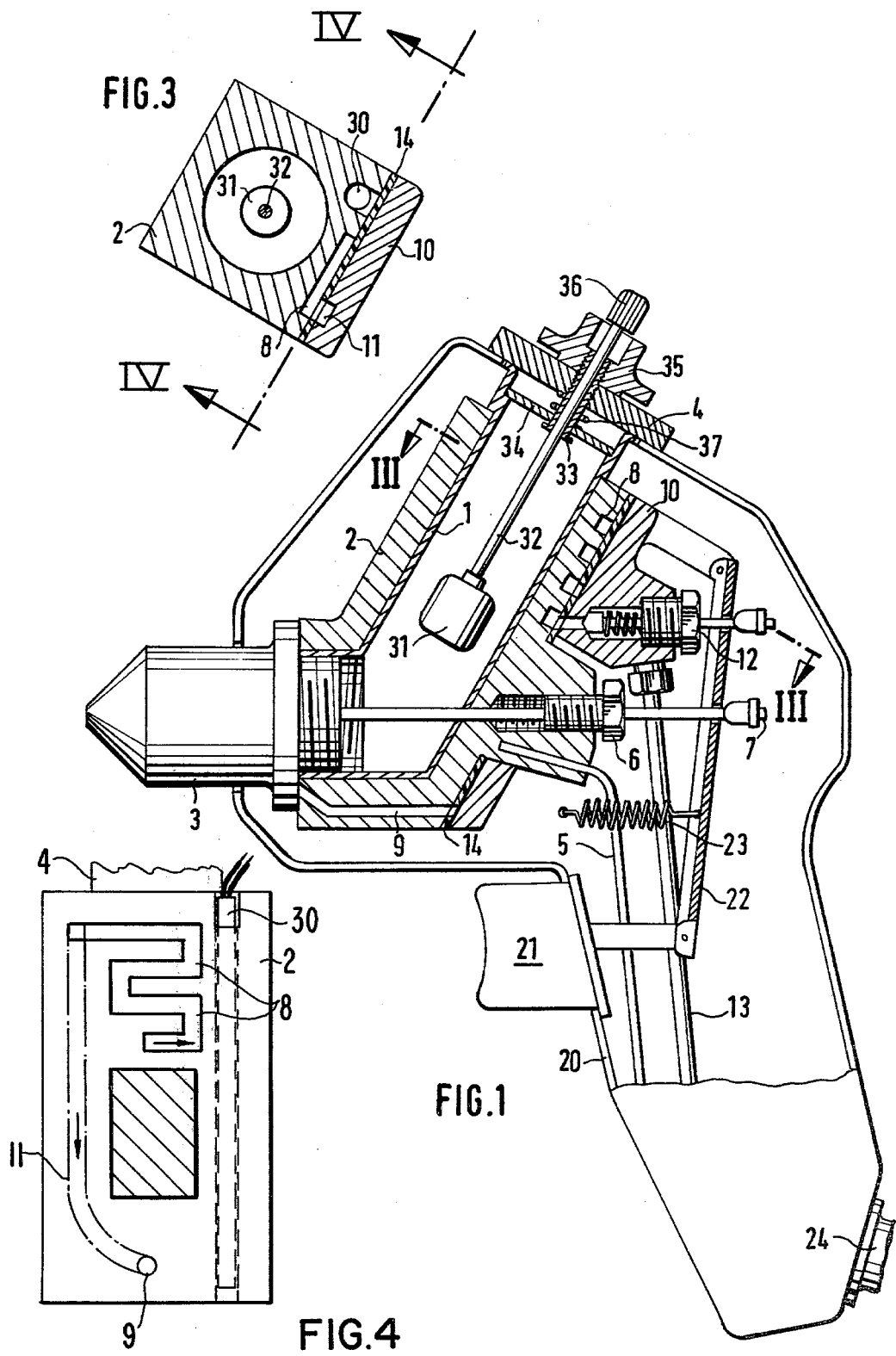
FIG. 1 is a simplified section through a metallizing gun.

A container 1, consisting of preferably stainless steel such as chromium steel, is cast in a block 2 of an aluminum alloy. The lower end of the container 1 is closed off by a nozzle 3 and the upper end is closed off by a cover 4 or closure member 34.

Bores are provided in block 2 for a temperature sensor 5 and a packing box or gland 6 which is traversed by a nozzle needle 7 which passes through the container 1 and extends into the nozzle 3. Furthermore, air ducts 8 and passages 9 are also provided in the block 2. The ducts 8 are covered by a cover 10 which in turn is also provided with ducts 11.

A duct for accommodating an electric heating element 30 is provided in the block 2 and extends parallel with respect to the container 1. This duct is covered by cover 10 in accordance with FIG. 3.

A spring-loaded air valve 12 is also provided in the cover 10 and attached to an air supply line 13. A seal 14 with appropriately located apertures is positioned between the cover 10 and the block 2. During operation, the air flows through the ducts 8, 11 and the passage 9 in such a way that it is heated before it arrives at the nozzle 3.

The drawing also illustrates a housing half 20 manufactured of plastic, an actuating button 21, an actuating lever 22 and a return spring 23.

An air feed hose, a cable for the current supply and measurement leads to the temperature sensor emerge from the housing at 24. The actuating button 21 is only indirectly connected with the hot parts of the gun by means of the lever 22 so that as little heat as possible is transmitted to the button 21.

In operation, the desired temperature of the alloy to be sprayed can be maintained exactly by electronic means and even the thermal inertia of the system can be taken into account.

As soon as the desired temperature is reached and the button 21 is actuated, the lever 22 is moved to the right, thereby causing the nozzle needle 7 to open the outlet opening for the molten alloy. At the same time, the air valve 12 is opened as well and hot air flows through the ducts and passageways 8, 11 and 9 to the nozzle 3 where it atomizes the molten metal to form droplets of metal.

A float 31 which is attached to the free end of a float needle 32 is located inside the container 1. The float needle 32 passes through a sleeve 33 on whose periphery the closure member 34 is displaceably mounted and which is pressed against an internal shoulder of the container 1 by means of a spring 37. For this purpose the spring 37 is located between the cover 4 and the closure member 34. Moreover, the cover 3 is associated with a closure element 35 which is held in position by the guide sleeve 33. A head 36 indicating the respective position of the float 31 is located at the free outwardly projecting end of the float needle. The head 36 thus reveals when the level of the molten metal has reached a minimum. Furthermore, the float 31 prevents in part the formation of an oxide on the surface of the molten metal. Such an oxide layer could result in the clogging or jamming of the nozzle 3.

Figure 2:
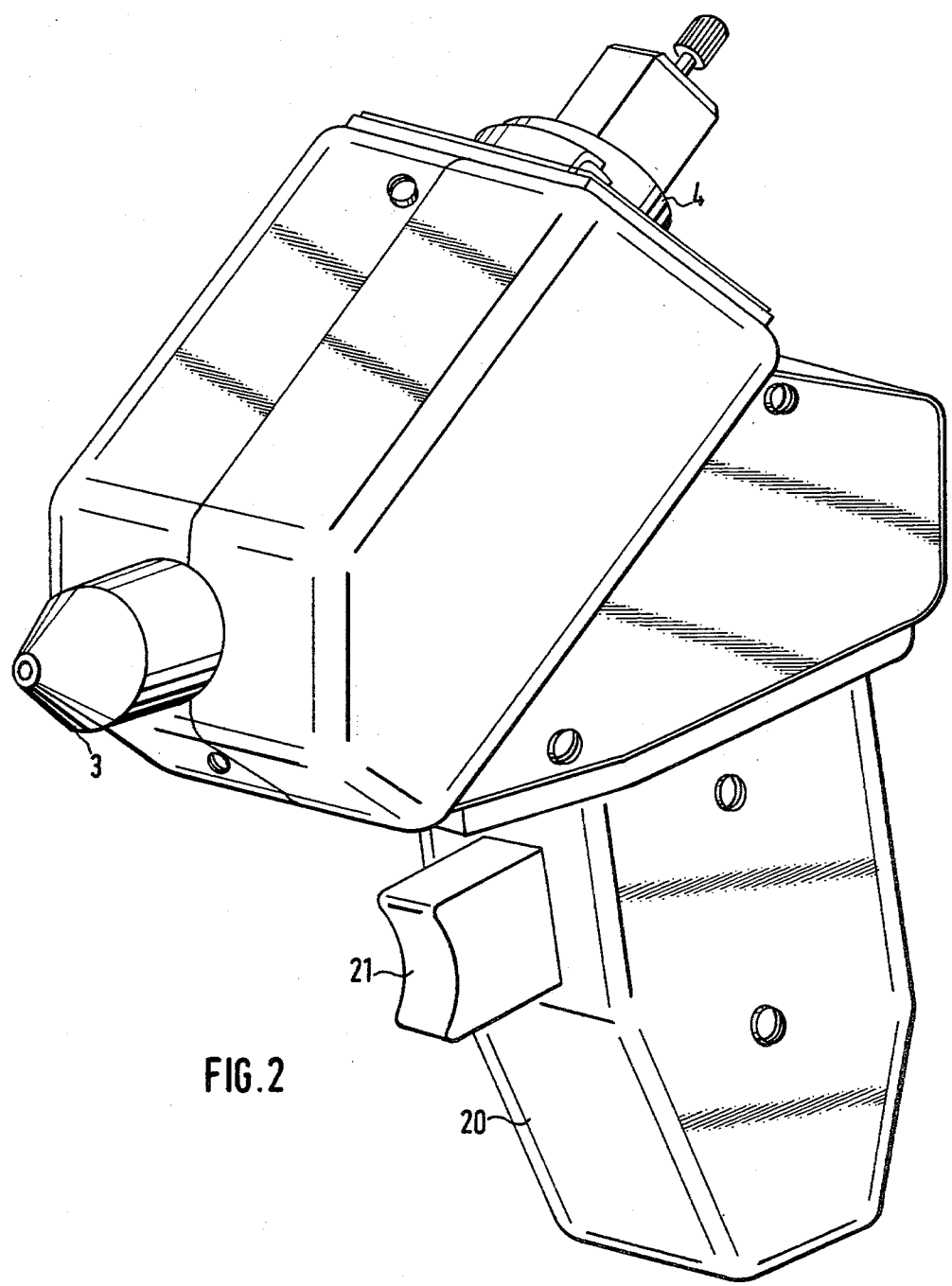
FIG. 2 is an external elevation of the metallizing gun in accordance with FIG. 1 in perspective.

The drawing has been simplified for the sake of clarity and the fastening and attachment elements which secure the cover 10 to the block 2 have been omitted. The fastening elements between the block 2 and the housing 20 as well as the thermal insulating material have been omitted as well. Omitted also were the fastening elements between the flange of the container 1 or block 2 and the cover 4. A few screws are visible in FIG. 2 which were used to fasten the housing halves 20 to the block 2.

The metallizing gun is employed in particular for making models in the field of dentistry. In so doing, the plaster impressions are sprayed with metal and are then subsequently filled (cast) with plaster, in particular plastic plaster, to produce working models.

What is claimed is:

1. An improved metallizing gun for applying sprayed metal which has a melting point below 350° C., which is liquified by an electric heating means provided in the metallizing gun and which is atomized in droplet form by preheated compressed air, wherein the improvement comprises a thinwalled steel container (1) for the liquid metal which is surrounded by a massive block (2) of a thermally conductive metal alloy, which contains an electric heating element (30) narrowly disposed within an elongated recess which recess extends parallel and adjacent to the wall of said steel container and a temperature sensor (5), the external side of said massive block including air ducts (8,11,9) which connect to the spray nozzle (3) and which transmit heat to said block (2).

2. A metallizing gun as recited in claim 1, wherein the thinwalled container (1) consists of chromium steel.

3. A metallizing gun as recited in claim 1, wherein the massive block (2) consists of an aluminum alloy.

4. A metallizing gun for applying sprayed metal which has a melting point below 350° C., which is liquified by an electric heating means provided in the metallizing gun and which is atomized in droplet form by preheated compressed air, further comprising a thinwalled container for the liquid metal which is surrounded by a massive block of a thermally conductive metal alloy, which contains an electric heating element narrowly disposed within an elongated recess which recess extends parallel and adjacent to the wall of said steel container and a temperature sensor, the external side of said massive block including air ducts which connect to the spray nozzle and which transmit heat to said block, wherein the massive block (2) is accommodated in a plastic housing (20) with an interposed layer of heat insulation material or air.

5. A metallizing gun for applying sprayed metal which has a melting point below 350° C., which is liquified by an electric heating means provided in the metallizing gun and which is atomized in droplet form by preheated compressed air, further comprising a thinwalled steel container for the liquid metal which is surrounded by a massive block of a thermally conductive metal alloy, which contains an electric heating element narrowly disposed within an elongated recess which recess extends parallel and adjacent to the wall of said steel container and a temperature sensor, the external side of said massive block including air ducts which connect to the spray nozzle and which transmit heat to the block, the massive block being accommodated in a plastic housing with an interposed layer of heat insulation material or air, wherein an actuating button (21) is operatively connected through an intermediate member (22) with a nozzle needle (7) and an air valve (12).

6. A metallizing gun for applying sprayed metal which has a melting point below 350° C., which is liquified by an electric heating means provided in the metallizing gun and which is atomized in droplet form by preheated compressed air, further comprising a thinwalled steel container for the liquid metal which is surrounded by a massive block of a thermally conductive metal alloy, which contains an electric heating element narrowly disposed within an elongated recess which recess extends parallel and adjacent to the wall of said steel container and a temperature sensor, the external side of said massive block including air ducts which connect to the spray nozzle and which transmit heat to the block, the massive block being accommodated in a plastic housing with an interposed layer of heat insulation material or air, an actuating button being operatively connected through an intermediate member with a nozzle needle and an air valve, wherein a float (31) located on a float needle (32) is located inside the container (1), said float needle being adjustably guided in the container cover (4).

7. An improved metallizing gun according to claim 1 wherein said heater is a cartridge type heater.

8. A process for applying metal to a surface which comprises spraying said surface with a metal from a metallizing gun comprising a thinwalled steel container for a liquid metal surrounded by a massive block of a thermally conductive metal alloy which spray gun contains an electric heating element narrowly disposed within an elongated recess which recess extends parallel and adjacent to the wall of said steel container and a temperature sensor, the external side of said massive block including air ducts which connect to a spray nozzle of said metallizing gun and which air ducts transmit heat to said block wherein said metal is initially maintained in said container, said massive block is heated by said heater at a temperature sufficient to liquify said metal and preheated compressed air is passed through said gun to atomize said metal.

9. A process according to claim 8 wherein said surface is a surface of a dental model.

10. A process according to claim 9 wherein said gun further comprises a plastic housing within which said massive block is accommodated, an insulating layer of heat insulating material or air disposed between said metal block and said plastic housing, an actuating button operatively connected through an intermediate member with a nozzle needle and air valve, a float located on a flat needle inside said container, the float needle being adjustably guided in a container cover.

* * * * *